US010286159B2

(12) United States Patent
Snoke et al.

(10) Patent No.: US 10,286,159 B2
(45) Date of Patent: May 14, 2019

(54) MEDICAL INJECTION ASSEMBLIES FOR ONABOTULINUMTOXINA DELIVERY AND METHODS OF USE THEREOF

(71) Applicant: URO-1, Inc., Winston-Salem, NC (US)

(72) Inventors: Phillip Jack Snoke, Winston-Salem, NC (US); Philip Morrison Allred, III, Kernersville, NC (US); John Joseph Smith, Winston-Salem, NC (US)

(73) Assignee: URO-1, INC., Winston-Salem, NC (US)

( * ) Notice: Subject to any disclaimer, the term of this patent is extended or adjusted under 35 U.S.C. 154(b) by 0 days.

(21) Appl. No.: 15/697,640

(22) Filed: Sep. 7, 2017

(65) Prior Publication Data

US 2019/0070366 A1    Mar. 7, 2019

(51) Int. Cl.
  *A61M 5/315*    (2006.01)
  *A61M 5/32*    (2006.01)
  *A61M 5/34*    (2006.01)
  *A61M 5/31*    (2006.01)

(52) U.S. Cl.
  CPC ...... *A61M 5/31581* (2013.01); *A61M 5/3134* (2013.01); *A61M 5/31525* (2013.01); *A61M 5/3287* (2013.01); *A61M 5/343* (2013.01)

(58) Field of Classification Search
  CPC ...... A61M 5/31581; A61M 2025/0089; A61M 2025/009; A61M 2025/0037; A61M 25/0041; A61M 25/0084
  See application file for complete search history.

(56) References Cited

U.S. PATENT DOCUMENTS

| 5,386,817 | A |   | 2/1995  | Jones |
|-----------|---|---|---------|-------|
| 5,435,805 | A |   | 7/1995  | Edwards |
| 5,486,161 | A | * | 1/1996  | Lax ............... A61B 10/0233 604/22 |
| 5,849,011 | A |   | 12/1998 | Jones |
| 5,873,877 | A |   | 2/1999  | McGaffigan |
| 5,993,447 | A |   | 11/1999 | Blewett |
| 6,059,734 | A | * | 5/2000  | Yoon ............... A61B 10/0275 600/565 |
| 6,106,521 | A |   | 8/2000  | Blewett |

(Continued)

OTHER PUBLICATIONS

"Compound Curve". Merriam-Webster.com. Merriam-Webster (accessed Feb. 21, 2018).*

*Primary Examiner* — Kevin C Sirmons
*Assistant Examiner* — Leah J Swanson
(74) *Attorney, Agent, or Firm* — Cooper & Dunham LLP

(57) ABSTRACT

A medical injection assembly is provided and includes an introducer with a handle, a sheath, and a scope lumen extending from a first proximal end of the handle to a distal end of the sheath, wherein the scope lumen is configured to receive an endoscope at the first proximal end of the handle and hold the endoscope in a desired position. The introducer includes a cannula lumen extending from a second proximal end of the handle to the distal end of the sheath, wherein the cannula lumen is configured to receive a cannula at the second proximal end of the handle and hold the cannula in a desired position. The medical injection assembly includes a cannula configured such that the distance between the distal tip of the cannula and the axis defined by the sheath of the introducer increases as the cannula is moved in a distal direction.

23 Claims, 9 Drawing Sheets

(56) References Cited

U.S. PATENT DOCUMENTS

| | | | | |
|---|---|---|---|---|
| 6,126,633 | A * | 10/2000 | Kaji | A61M 25/0084 604/164.01 |
| 6,296,633 | B1 * | 10/2001 | Helgerson | A61M 25/0009 606/1 |
| 6,428,538 | B1 | 8/2002 | Blewett | |
| 6,855,124 | B1 * | 2/2005 | Gonzalez | A61B 17/3478 604/164.1 |
| 6,905,475 | B2 | 6/2005 | Hauschild | |
| 8,394,068 | B2 * | 3/2013 | Kosinski | A61M 5/31511 604/187 |
| 8,874,781 | B2 | 10/2014 | Avitsian | |
| 2003/0032929 | A1 * | 2/2003 | McGuckin, Jr. | A61B 17/3417 604/272 |
| 2004/0013652 | A1 | 1/2004 | Marko | |
| 2008/0058595 | A1 * | 3/2008 | Snoke | A61B 1/00135 600/114 |
| 2008/0177225 | A1 * | 7/2008 | Matsumoto | A61M 5/1785 604/82 |
| 2012/0259203 | A1 * | 10/2012 | Devereux | A61M 25/0631 600/414 |
| 2014/0200402 | A1 * | 7/2014 | Snoke | A61B 17/42 600/104 |
| 2015/0150690 | A1 * | 6/2015 | Schaller | A61B 17/8852 623/17.16 |
| 2016/0166772 | A1 * | 6/2016 | Mirzazadeh | A61M 5/31526 604/222 |

* cited by examiner

MEDICAL INJECTION ASSEMBLIES FOR ONABOTULINUMTOXINA DELIVERY AND METHODS OF USE THEREOF

BACKGROUND

Approximately 16.0% of the United States population suffers from Overactive Bladder (OAB). Because OAB is a chronic condition, treatments must be administered on a periodic basis to control the systems. Injections of OnabotulinumtoxinA, marketed under the trade name Botox, have proven effective in treating OAB for longer periods of time with low incidence of adverse events. Current methods of delivering OnabotulinumtoxinA to the bladder involve inserting a cystoscope and needle through the urethra to the bladder and manipulating the entire assembly both laterally and along the axis of the urethra as a unit to inject the medication into the bladder wall. Because the cystoscope and needle are moved together during this procedure, current devices and their methods of use result in significant patient discomfort and possible damage to the urethra.

The placement and pattern of the multiple injections in the bladder are associated with significantly improved treatment outcomes. Thus, it is important that devices and methods of injecting OnabotulinumtoxinA into the bladder offer physicians performing the procedure precise control. However, it is difficult to create precise injection patterns using current devices and methods because the scope moves with the needle when aiming for a new injection site. Moreover, said devices are usually not disposable, and must be disassembled and sterilized after each use, making them difficult to maintain and increasing the risk of contamination or infection.

What is needed, therefore, is a device that can inject OnabotulinumtoxinA in precise patterns on the bladder wall while minimizing lateral movement of the device itself while in the urethra to decrease patient discomfort and probability of urethral injury. Furthermore, said device should be simple enough to keep manufacturing costs at a minimum so that the device may be disposable.

SUMMARY OF THE INVENTION

The present invention relates to a medical injection assembly directed towards the treatment of Overactive Bladder by injecting OnabotulinumtoxinA into bladder tissue. The present invention is also directed towards a flexible cannula with high tensile strength and buckling resistance for use in said medical injection assemblies. The present invention is also directed towards novel incremental syringe plungers for the highly precise delivery of OnabotulinumtoxinA in said medical injection assemblies.

In one embodiment of the present invention, a medical injection assembly may include an introducer. The introducer may include a handle, a sheath, and a scope lumen extending from a first proximal end of the handle to a distal end of the sheath, wherein the scope lumen is configured to receive an endoscope at the first proximal end of the handle and hold the endoscope in a desired position. The introducer may further include a cannula lumen extending from a second proximal end of the handle to the distal end of the sheath, wherein the cannula lumen is configured to receive a cannula at the second proximal end of the handle and hold the cannula in a desired position. The introducer may further include a fluid line, wherein the distal end is in fluid communication with the scope lumen. The medical injection assembly may further include a cannula configured such that the distance between the distal tip of the cannula and the axis defined by the sheath of the introducer increases as the cannula is moved in a distal direction. The medical injection assembly may further include a syringe connected to the proximal end of the cannula.

In one embodiment of the present invention, the cannula may include a needle attached to a distal tip of the cannula. The cannula may further include a first fluid connector attached to a proximal end of the cannula. The cannula may be comprised of a biocompatible thermoplastic polymer and a distal portion of the cannula may maintain a predefined curvature in the absence of a deforming force.

In one embodiment of the present invention, wherein the diameter of the needle is less than the diameter of the cannula.

In one embodiment of the present invention, the needle may be a 23 gauge needle.

In one embodiment of the present invention, the biocompatible thermoplastic polymer may have a flexural modulus of about 595,000 psi.

In one embodiment of the present invention, the biocompatible thermoplastic polymer may be polyether ether-ketone (PEEK).

In one embodiment of the present invention, the predefined curvature may be defined by an inverse tangent function.

In one embodiment of the present invention, the medical injection assembly may further include an endoscope.

In one embodiment of the present invention, the endoscope may be a cystoscope.

In one embodiment of the present invention, the fluid line may further comprise a second fluid connector, and the fluid line may further comprise a pinch valve to control flow of fluid through the fluid line.

In one embodiment of the present invention, the syringe may include a syringe barrel and a plunger body having a first portion proximate the proximal end and a second portion proximate the distal end, wherein the first portion has a plurality of corresponding detentes on opposite sides of the first portion. The plunger body may further include a sealing cap attached to the distal end of the plunger body. The syringe may further include a finger grip including two paddles. The finger grip may be configured to be removably coupled to the plunger body and may further be configured to interact with the detentes to provide audible and tactile feedback to a user when the plunger body is pushed through the finger grip in a distal direction.

In one embodiment of the present invention, a method for treating overactive bladder may include inserting an endoscope into a scope lumen of an introducer. The method may further include inserting a cannula into a cannula lumen of the introducer, the cannula configured such that the distance between the distal tip of the cannula and the axis defined by the sheath of the introducer increases as the cannula is moved in a distal direction, wherein a syringe filled with OnabotulinumtoxinA is coupled to the proximal end of the cannula. The method may further include guiding the introducer through the urethra of a patient to the patient's bladder. The method may further include extending the distal portion of the cannula past the distal end of the introducer until a needle attached to the distal end of the cannula is placed at a desired radial distance from the axis defined by the sheath of the introducer. The method may further include rotating the introducer to position the needle at a desired position. The method may further include moving the introducer in a distal direction to insert the needle into the bladder. The method may further include activating the syringe to inject OnabotulinumtoxinA into the bladder. The method may further include moving the introducer in a proximal direction to remove the needle from the bladder. The method may further include repeating the extending, rotating, moving distally, activating, and moving proximally steps until a therapeutically effective amount of OnabotulinumtoxinA has been injected in a therapeutically effective pattern into the bladder.

Still other aspects, features, and advantages of the invention are readily apparent from the following detailed description when illustrated by a number of particular embodiments and implementations, including the best mode contemplated for carrying out the invention. The invention is also capable of other and different embodiments, and several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

These and other objects, features, and characteristics will become more apparent to those skilled in the art from a study of the following Detailed Description in conjunction with the appended claims and drawings, all of which form a part of this specification. While the accompanying drawings include illustrations of various embodiments, the drawings are not intended to limit the claimed subject matter.

DETAILED DESCRIPTION

In the following description, for the purposes of explanation, numerous specific details are set forth in order to provide a thorough understanding of the embodiments of the invention. One skilled in the art will recognize that the embodiments of the invention may be practiced without these specific details or with an equivalent arrangement. In other instances, well-known structures and devices are shown in block diagram form in order to avoid unnecessarily obscuring the embodiments of the invention.

The presently disclosed subject matter is presented with sufficient details to provide an understanding of one or more particular embodiments of broader inventive subject matters. The descriptions expound upon and exemplify particular features of those particular embodiments without limiting the inventive subject matters to the explicitly described embodiments and features. Considerations in view of these descriptions will likely give rise to additional and similar embodiments and features without departing from the scope of the presently disclosed subject matter.

Figure 1:
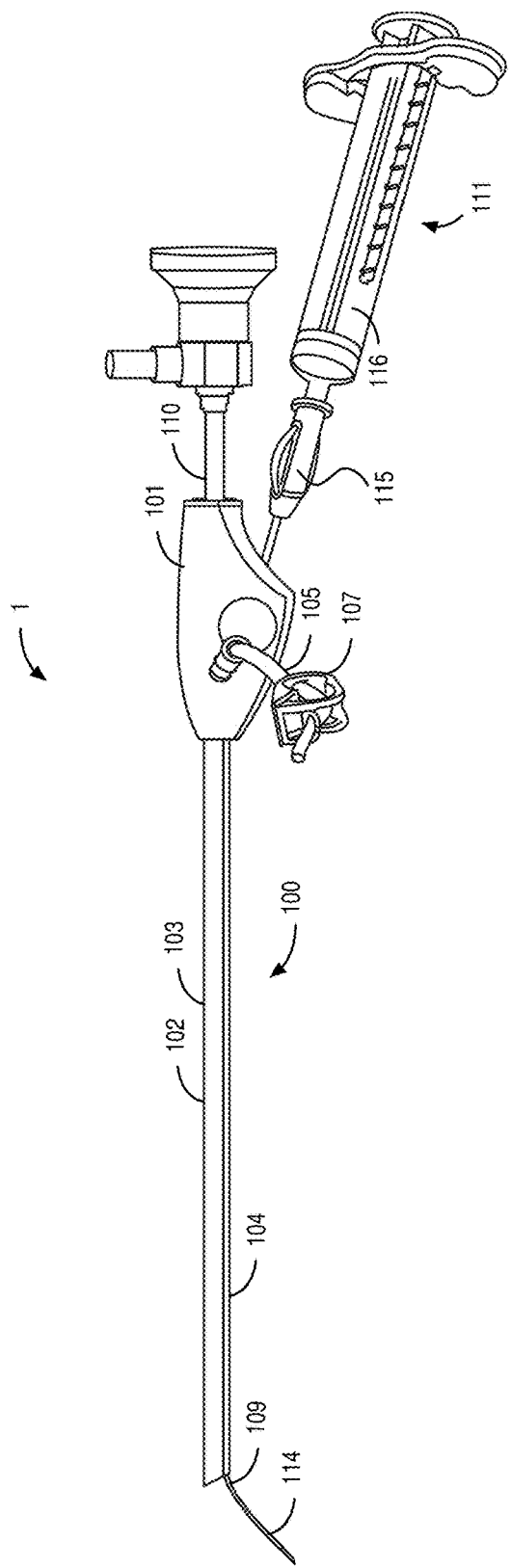
FIG. 1 is a side view of a medical injection assembly according to one embodiment of the present invention.

Referring now to FIG. 1, a medical injection assembly 1 according to an embodiment of the present invention is shown. The medical injection assembly 1 may comprise an introducer 100. The introducer may comprise a handle 101, and sheath 102, a scope lumen 103 extending from a first proximal end of the handle 101 to a distal end of the sheath 102, wherein the scope lumen 103 is configured to receive an endoscope 110 at the first proximal end of the handle 101 and hold the endoscope in a desired position, and a cannula lumen 104 extending from a second proximal end of the handle 101 to the distal end of the sheath 102, wherein the cannula lumen 104 is configured to receive a cannula 109 at the second proximal end of the handle 101 and hold the cannula 109 in a desired position. The introducer 100 may further comprise a fluid line 105, wherein the distal end is in fluid communication with the scope lumen 103.

The medical injection assembly 1 may further comprise a cannula 109 configured such that the distance between the distal tip of the cannula 109 and the axis defined by the sheath 102 of the introducer increases as the cannula 109 is moved in a distal direction. The medical injection assembly may further comprise a syringe 111 connected to the proximal end of the cannula 109.

The fluid line 105 may further comprise a second fluid connector 106. The fluid line 105 may further comprise a pinch valve 107 configured to control flow of fluid through the fluid line 105.

Figure 2:
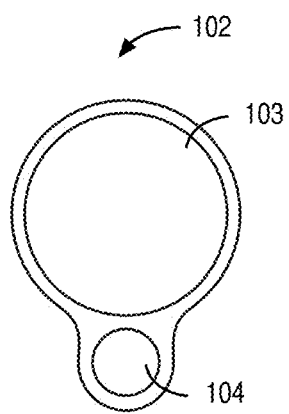
FIG. 2 is a cross-section of a sheath of an introducer according to one embodiment of the present invention.
Figure 3:
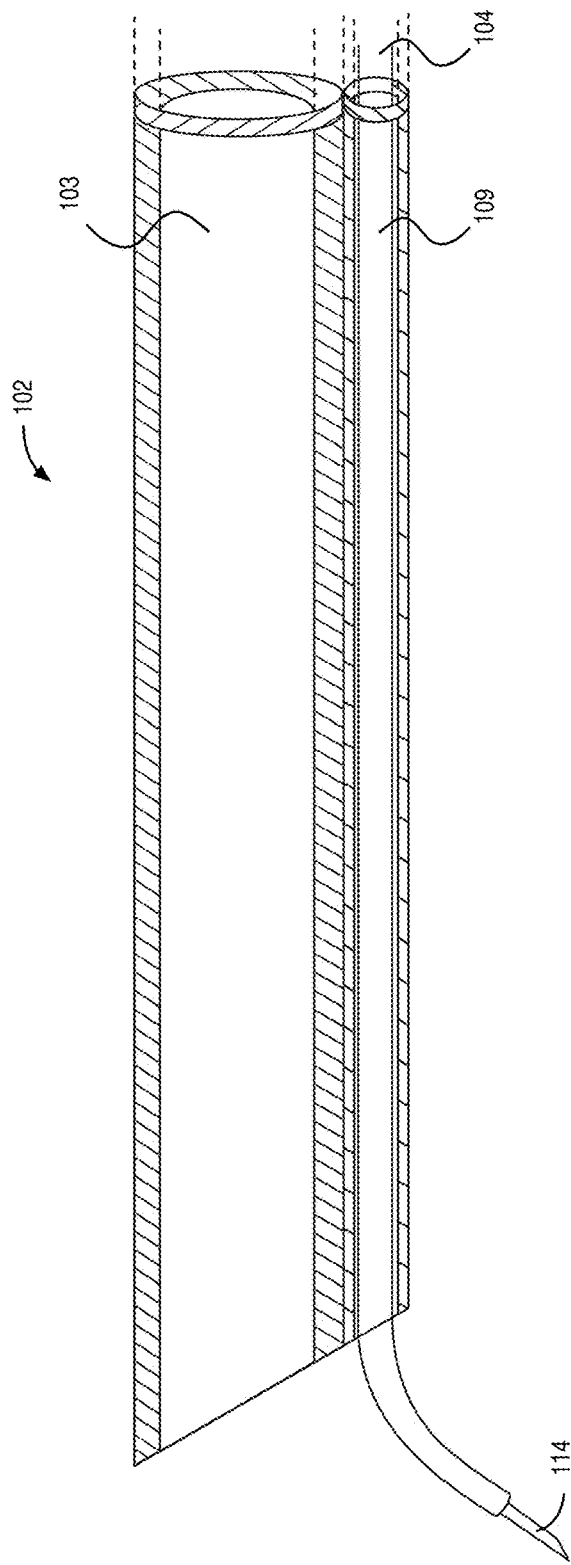
FIG. 3 is a cut-away isometric view of a sheath of an introducer according to one embodiment of the present invention.

Referring now to FIGS. 2 and 3, the sheath 102 of an introducer 100 according to an embodiment of the present invention is shown. Scope lumen 103 may be configured to receive a variety of endo scopes 110 for illuminating and visualizing target tissue within the body. In preferred embodiments, the endoscope 110 may be a cystoscope. The diameter of the scope lumen 103 should be sufficient to fit industry standard cystoscopes known in the art. In preferable embodiments, the scope lumen 103 may have a diameter of about 4 mm to about 5 mm.

The cannula lumen 104 may be configured to receive a cannula 109 according to the present invention as further described herein. The diameter of the cannula lumen 104 should be sufficient to fit said cannulas 109. In preferred embodiments, the cannula lumen 104 may have a diameter of about 1 mm to about 2 mm. The walls of the sheath 102 are must be minimized so as to allow the introducer 100 to fit through a patient's urethra while maintaining its strength and rigidity. In preferred embodiments, the sheath walls may have a thickness of about 0.1 mm to about 0.4 mm. The sheath 102 may be comprised of polyether block amides, polyethylene, or other materials with similar rigidity characteristics.

Figure 4:
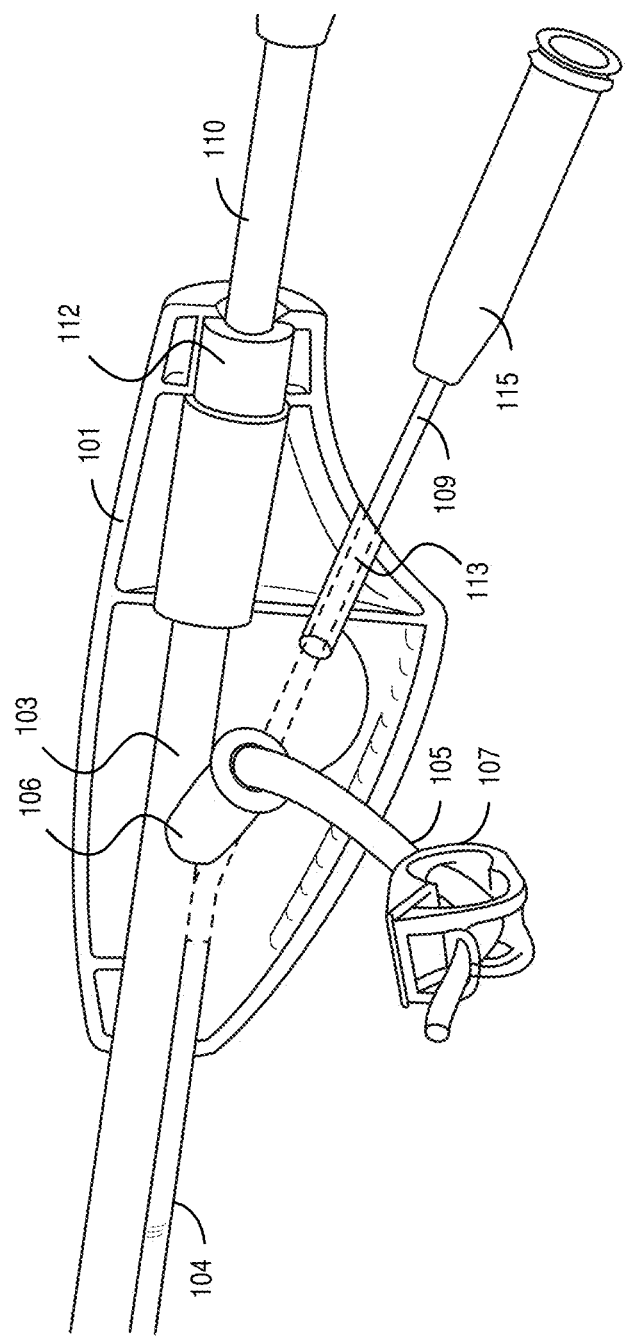
FIG. 4 is a cross-section of a handle of an introducer according to one embodiment of the present invention.

Referring now to FIG. 4, a cross-section of the handle 101 of an introducer 100 according to an embodiment of the present invention is shown. The scope lumen 103 may extend from a proximal end of the handle 101 and may be configured to receive an endoscope 110 from a proximal end of the handle 101. A scope seal 112 may be positioned at a proximal end of the handle 101 to engage an endoscope 110. The scope seal 112 may be comprised of a material with coefficient of friction sufficient to hold an endoscope 110 in place. In preferable embodiments, the scope seal 112 may be comprised of silicone.

The cannula lumen 104 may extend from a proximal end of the handle 101 and may be configured to receive a cannula 109 from a proximal end of the handle 101. A cannula seal 113 may be positioned at a proximal end of the handle 101 to engage a cannula 109. The cannula seal 113 may be comprised of a material with coefficient of friction sufficient to hold a cannula 109 in place. In preferable embodiments, the cannula seal 113 may be comprised of silicone.

The handle may further comprise a fluid line 105 in fluid communication with the scope lumen 103. The distal end of the fluid line 105 may connect to the scope lumen 103 via a watertight fluid connector. In yet other embodiments, the distal end of the fluid line 105 may be integrated directly into the scope lumen 103 via known manufacturing methods such as various molding techniques, welding, 3D printing, adhesives, etc. The fluid line 105 may comprise a second fluid connector 106. In preferred embodiments, the second fluid connector 106 may be a luer lock. The fluid line 105 may further comprise a pinch valve 107. The pinch valve 107 may control the flow of fluid form a fluid source through the fluid line 105 and into the scope lumen 103.

Figure 5A:
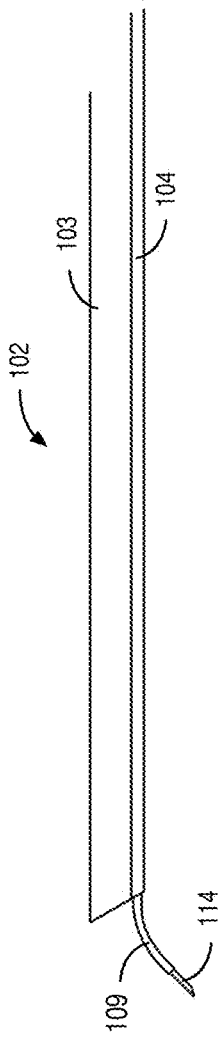
FIG. 5A is a side view of a cannula exiting a sheath of an introducer according to one embodiment of the present invention.
Figure 5B:
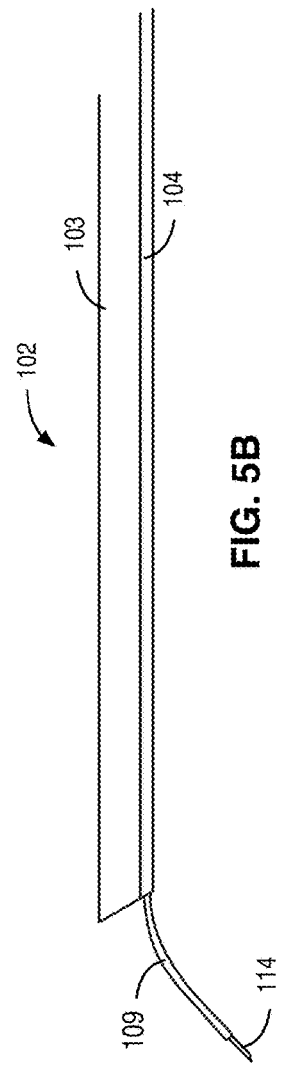
FIG. 5B is a side view of a cannula exiting a sheath of an introducer according to one embodiment of the present invention.
Figure 5C:
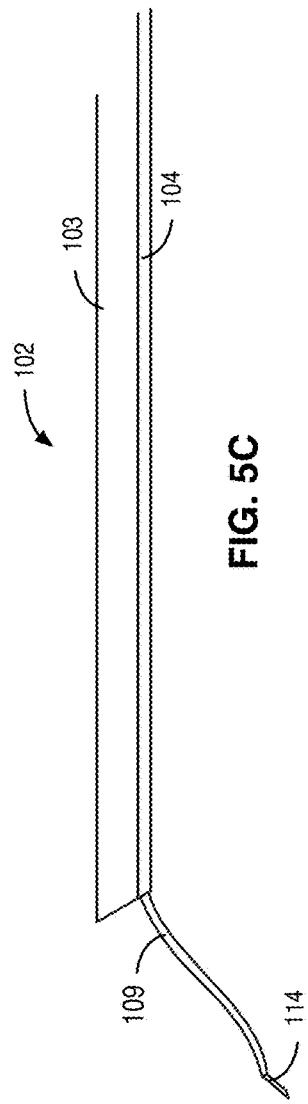
FIG. 5C is a side view of a cannula exiting a sheath of an introducer according to one embodiment of the present invention.

Referring now to FIGS. 5A-5C, a cannula 109 according to an embodiment of the present invention in use is shown. The cannula 109 may comprise a needle 114 attached to a distal tip of the cannula 109. The cannula 109 may further comprise a first fluid connector 115 attached to a proximal end of the cannula 109, wherein the cannula 109 may be comprised of a biocompatible thermoplastic polymer, and wherein a distal portion of the cannula 109 may maintain a predefined curvature in the absence of a deforming force.

The needle 114 may be any commercially available hypodermic needle suitable for performing injections of OnabotulinumtoxinA. In preferred embodiments, the diameter of the needle 114 is less than the diameter of the cannula 109, and the needle 114 may be a 23 gauge needle and may extend past the cannula 109 about 1.0 mm to about 3.0 mm in length. In such configurations, the distal tip of the cannula 109 acts as a wall, preventing the needle 114 from penetrating into the target tissue past the distal tip of the cannula 109.

The biocompatible thermoplastic polymer may be any such polymer having a flexural modulus of about 595,000 psi. Importantly, such a flexural modulus allows the user of the device to insert the needle into bladder tissue without causing the cannula itself to bend or deform in a clinically significant manner. In preferred embodiments, the biocompatible thermoplastic polymer may be polyether ether-ketone (PEEK).

The cannula 109 may be configured such that the distance between the distal tip of the cannula 109 and the axis defined by the sheath 102 of the introducer 100 increases as the cannula 109 is moved in a distal direction. According to at least one embodiment of the present invention, such a configuration may be achieved by forming the cannula 109 such that a distal portion of the cannula 109 maintains a predefined curvature in the absence of a deforming force. Thus, as the distal portion of the cannula 109 exits the distal end of the introducer 100, it returns to a predefined curvature that causes the distal tip of the cannula 109 to move away from the axis defined by the sheath 102 of the introducer 100. In preferred embodiments, the predefined curvature may be defined by an inverse tangent function. But one of ordinary skill in the art will recognize that any predefined curvature that causes the distal tip of the cannula 109 to move away from the axis defined by the sheath 102 of the introducer 100 may be used in the present invention.

Figure 6:
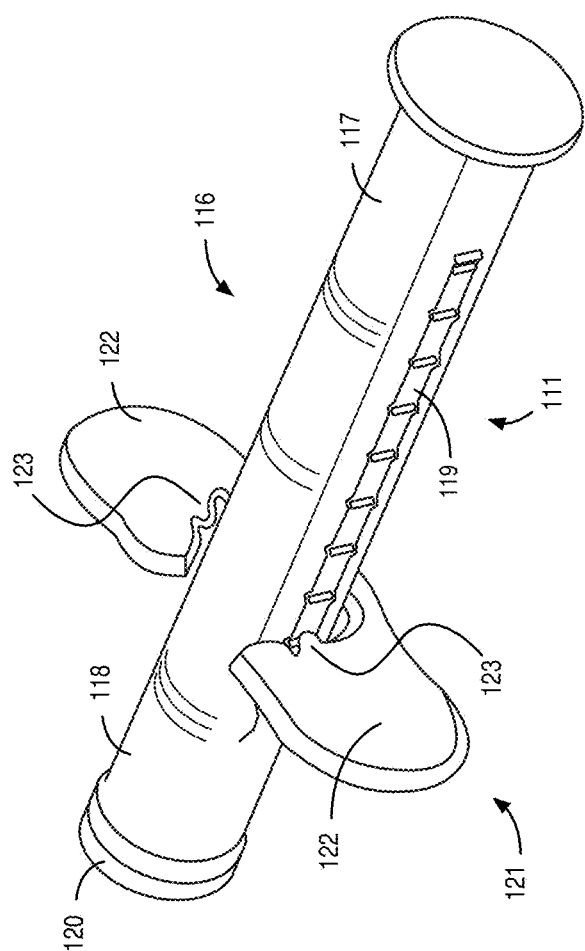
FIG. 6 is an isometric view of a plunger body according to one embodiment of the present invention.
Figure 7:
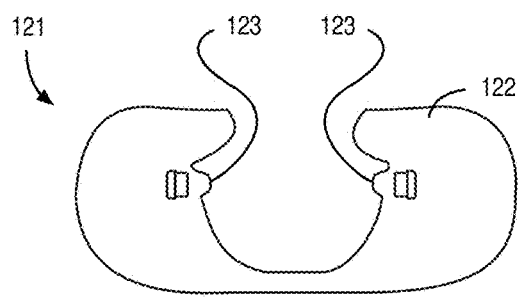
FIG. 7 is a bird's eye view of a finger grip according to one embodiment of the present invention.

Referring now to FIGS. 6-7, the syringe 111 may comprise a syringe barrel. The syringe 111 may also comprise a plunger body 116 having a first portion 117 proximate the proximal end and second portion 118 proximate the distal end, wherein the first portion 117 has a plurality of corresponding detentes 119 on opposite sides of the first portion 117. The syringe 111 may also comprise a sealing cap 120 attached to the distal end of the plunger body 116 and a finger grip 121 comprising two paddles 122. The finger grip may be configured to be removably coupled to the plunger body 116 and to interact with the detentes 119 to provide audible and tactile feedback to a user when the plunger body 116 is pushed through the finger grip 121 in a distal direction.

The second portion 118 may fit into commercially available syringe barrels with the sealing cap 120 forming a watertight seal within the syringe barrel. In preferred embodiments, commercially available 10 cc syringe barrels may be used. The finger grip 121 may be configured to clip on to the plunger body 116. The finger grip 121 may include tabs 123 on the interior of both paddles 122. The tabs 123 may fit into grooves between the detentes 119 on the first portion 117. When the user pushes the plunger body 116 in a distal direction into the syringe barrel, the detentes 119 provide resistance against the movement until the tabs 123 bend enough to clear a set of detentes 119 and fit into the next set of grooves. The detentes 119 may be spaced along the first portion 117 such that clearing one set of detentes 119 results in an ejection of a specific amount of fluid from the syringe. In preferred embodiments, clearing one set of detentes would result in the ejection of 1 cc of fluid from the syringe. When the user causes tabs 123 to clear a set of detentes 119 and the tabs 123 come to rest in the subsequent grooves, the user is provided with tactile and audible feedback to indicate that one such predetermined unit of fluid has been ejected from the syringe.

According to another embodiment of the present invention, a method for treating overactive bladder may comprise inserting an endoscope 110 into a scope lumen 103 of an introducer 100. The method may further comprise inserting a cannula 109 into a cannula lumen 104 of the introducer 100, the cannula 109 configured such that the distance between the distal tip of the cannula 109 and the axis defined by the sheath 102 of the introducer 100 increases as the cannula 109 is moved in a distal direction, wherein a syringe 111 filled with OnabotulinumtoxinA is coupled to the proximal end of the cannula 109. The method may further comprise guiding the introducer 100 through the urethra of a patient to the patient's bladder. The method may further include extending the distal portion of the cannula 109 past the distal end of the introducer 100 until a needle 114 attached to the distal end of the cannula 109 is placed at a desired radial distance from the axis defined by the sheath of the introducer. The method may further comprise rotating the introducer 100 to position the needle 114 at a desired position. The method may further comprise moving the introducer in a distal direction to insert the needle 114 into the bladder. The method may further include activating the syringe 111 to inject OnabotulinumtoxinA into the bladder. The method may further include moving the introducer 100 in a proximal direction to remove the needle 114 from the bladder. The method may further include repeating the extending, rotating, moving distally, activating, and moving proximally steps until a therapeutically effective amount of OnabotulinumtoxinA has been injected in a therapeutically effective pattern into the bladder.

Figure 8A:
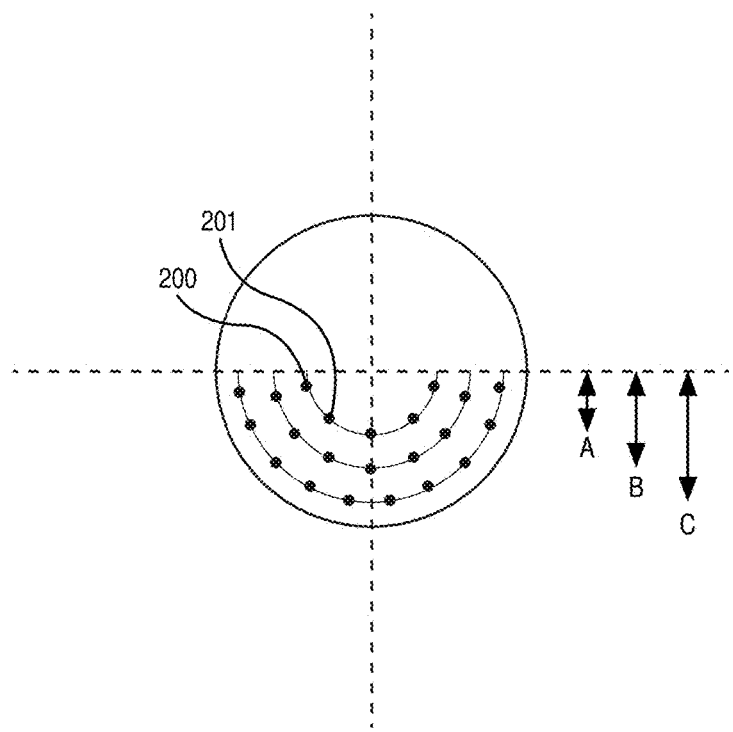
FIG. 8A is a frontal view diagram of a bladder injection pattern according to one embodiment of the present invention.
Figure 8B:
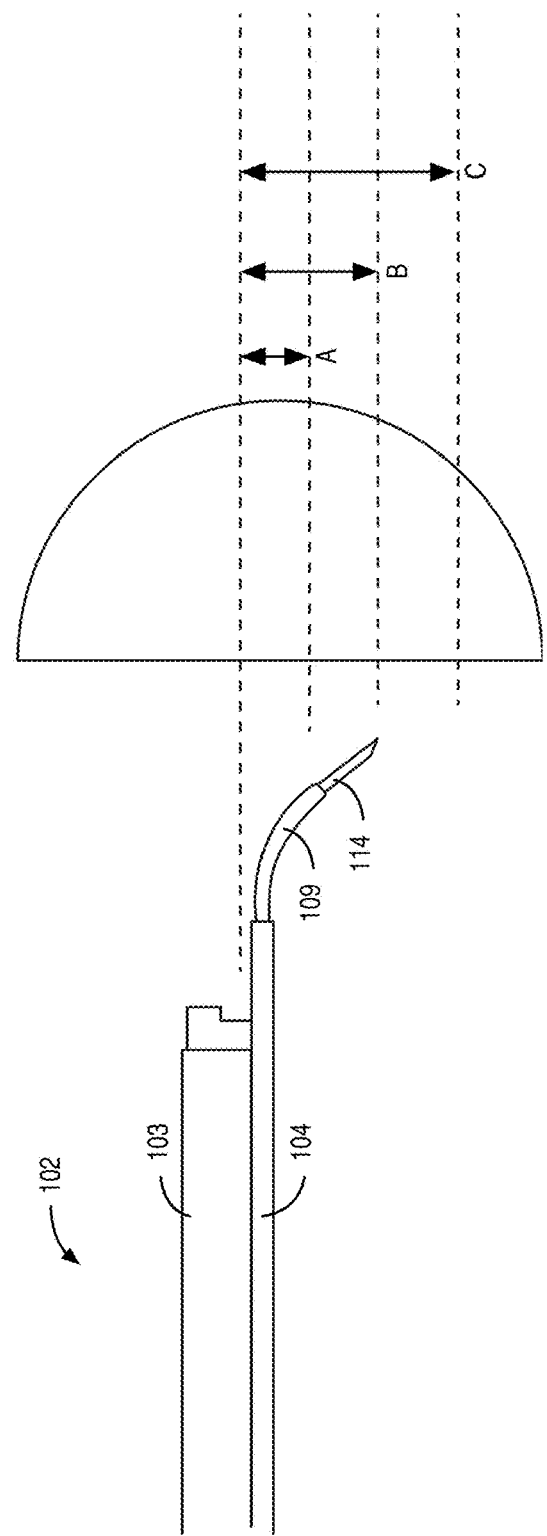
FIG. 8B is a side view diagram of a bladder injection pattern according to one embodiment of the present invention.

Referring now to FIGS. 8A-8B, therapeutically effective patterns of injections according to at least one embodiment of the present invention is shown. It is beneficial to disperse the injections of OnabotulinumtoxinA across the bladder tissue. In preferred embodiments, injections patterns may comprise three concentric semi-circles in the lower half of the bladder with radii A, B, and C. Such an injection pattern may be created by moving the cannula 109 distally until the needle 114 is at a distance A from the axis defined by the sheath 102 of the introducer 100. The introducer 100 may then be rotated until the needle 114 is at injection site 200. The introducer 100 may be moved distally to inject the bladder with OnabotulinumtoxinA and then moved proximally to withdraw the needle 114 from the bladder. The introducer 100 may then be rotated counterclockwise until the needle 114 is at injection site 201, and the injection process may be repeated. Once the injection pattern for the semi-circle with radius A is complete, the cannula 109 may be moved distally until the needle 114 is at a distance B from the axis defined by the sheath 102 of the introducer 100, and the previous steps may be repeated to create the injection patterns for the semi-circles with radii B and C.

Preferably, A is approximately 0.43 inches, B is approximately 0.8 inches, and C is approximately 1.2 inches.

By rotating the introducer 100 to position the needle rather than moving the introducer 100 laterally, the patient experiences less discomfort and possible injury from lateral stretching of the urethra.

The above description and drawings are illustrative and are not to be construed as limiting the invention to the precise forms disclosed. Persons skilled in the relevant art can appreciate that many modifications and variations are possible in light of the above disclosure. Numerous specific details are described to provide a thorough understanding of the disclosure. However, in certain instances, well-known or conventional details are not described in order to avoid obscuring the description.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or any combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The teachings of the disclosure provided herein can be applied to other systems, not necessarily the system described above. The elements and acts of the various embodiments described above can be combined to provide further embodiments.

These and other changes can be made to the disclosure in light of the above Detailed Description. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features, or aspects of the disclosure with which that terminology is associated. In general, the terms used in the following claims should not be construed to limit the disclosure to the specific embodiments disclosed in the specification, unless the above Detailed Description section explicitly defines such terms. Accordingly, the actual scope of the disclosure encompasses not only the disclosed embodiments, but also all equivalent ways of practicing or implementing the disclosure under the claims.

The terms used in this specification generally have their ordinary meanings in the art, within the context of the disclosure, and in the specific context where each term is used. Certain terms that are used to describe the disclosure are discussed above, or elsewhere in the specification, to provide additional guidance to the practitioner regarding the description of the disclosure. For convenience, certain terms may be highlighted, for example using capitalization, italics and/or quotation marks. The use of highlighting has no influence on the scope and meaning of a term; the scope and meaning of a term is the same, in the same context, whether or not it is highlighted. It will be appreciated that same element can be described in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions will control.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example reference to "an additive" can include a plurality of such additives, and so forth.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments +/−20%, in some embodiments, +/−10%, in some embodiments +/−5%, in some embodiments +/−1%, in some embodiments +/−0.5%, and in some embodiments, +/−0.1%, from the specified amount, as such variations are appropriate in the disclosed products and methods.

The invention claimed is:

1. A medical injection assembly for injecting onabotulinumtoxina at plural injection sites in a patient's bladder wall to alleviate an overactive bladder condition, without requiring a lateral motion that may stretch the patient's urethra, said assembly comprising:

an introducer configured for insertion into the patient's bladder through the urethra and having a cannula lumen;

a hollow cannula that is made of a biocompatible thermoplastic polymer and is inserted in said cannula lumen for sliding motion therein;

a hollow injection needle affixed to and extending distally from a distal tip of said cannula;

wherein a distal portion of said cannula:

(i) extends along a straight axis when in the cannula lumen and (ii) progressively returns to a predefined curvature defined by an inverse tangent function that it had before being inserted in the cannula lumen, as the cannula moves distally relative to the introducer and the cannula tip distally moves out of and away from the cannula lumen; and wherein a radial distance from the cannula tip to said axis changes as the cannula tip moves distally away from said cannula lumen;

wherein said injection needle points to injection sites in the bladder wall that are radially spaced from each other depending on a distance by which the cannula tip and said needle have moved away distally from said cannula lumen and are circumferentially spaced from each other depending on rotation of at least one of the introducer and cannula, without requiring a lateral introducer motion relative to the patient's urethra that may stretch the patient's urethra; and wherein said distal portion of the cannula has a flexural modulus sufficient for inserting said injection needle into the bladder wall at said plural injection sites, including when said distal portion of said cannula has returned to said curvature defined by an inverse tangent function, but is sufficiently flexible to extend along said straight axis when in the cannula lumen.

2. The medical injection assembly of claim 1, further including a syringe operatively coupled with said cannula and configured to inject through said cannula and needle a succession of predetermined amounts of said onabotulinumtoxina and to provide both an audible and a tactile indication for each of said amounts.

3. The medical injection assembly of claim 2, in which said syringe comprises a plunger body with detents along a length thereof, tabs configured to slide along said plunger and provide said indications by engaging with and disengaging from said detents, and laterally extending paddles configured to slide, with said tabs, along said plunger and provide a finger grip to facilitate pushing the plunger for motion relative to the tabs and paddles.

4. The medical injection assembly of claim 1, which said introducer further comprises an endoscope lumen configured to accept an endoscope for viewing the bladder.

5. The medical injection assembly of claim 4, further comprising a scope seal positioned at a proximal portion of said endoscope lumen, said scope seal being comprised of a material with a coefficient of friction sufficient to hold in place an endoscope inserted in said endoscope lumen to view the bladder.

6. The medical injection assembly of claim 1, further comprising a cannula seal positioned at a proximal portion of said cannula lumen, said cannula seal being comprised of a material with a coefficient of friction sufficient to hold said cannula in place.

7. The medical injection assembly of claim 1, in which said cannula is made of a polyether ether-ketone (PEEK).

8. A medical injection assembly comprising:

an introducer having a cannula lumen;

a hollow cannula at least a distal portion of which is made of a biocompatible thermoplastic polymer and is slidingly received in said cannula lumen;

a hollow injection needle affixed to and extending distally from a distal tip of said cannula;

said distal portion of the cannula being configured to maintain a first shape when subjected to a deforming force exerted thereon by said cannula lumen but to progressively return to a predefined curvature that is defined by an inverse tangent function and is different from said first shape as said distal tip of the cannula moves distally out of and away from said cannula lumen when the cannula is pushed in a distal direction relative to the cannula lumen;

wherein a radial distance from said cannula tip to a long axis of the cannula lumen changes depending on a distal motion of said tip and injection needle out of and away from the cannula lumen; and wherein said distal portion of the cannula has a flexural modulus sufficient for inserting the needle into a bladder wall for injecting at plural injection sites, including when the distal portion of the cannula has returned to said curvature defined by an inverse tangent function, but is sufficiently flexible to assume said first shape when in the cannula lumen.

9. The medical injection assembly of claim 8, in which at least a portion of the cannula lumen matching in length said distal portion of the cannula extends along a linear axis.

10. The medical injection assembly of claim 8, in which said biocompatible thermoplastic polymer is a polyether ether-ketone (PEEK).

11. The medical injection assembly of claim 8, further including a syringe operatively coupled with said cannula and configured to inject a succession of predetermined amounts of onabotulinumtoxina through said cannula and needle and to provide both an audible and a tactile indication for each of said amounts.

12. The medical injection assembly of claim 11, in which said syringe comprises a plunger body with detents along a length thereof, tabs configured to slide along said plunger and provide said indications by engaging with and disengaging from said detents, and laterally extending paddles configured to slide along said plunger with said tabs and provide a finger grip to facilitate pushing the plunger for motion relative to the tabs and paddles.

13. The medical injection assembly of claim 12, in which said introducer further comprises an endoscope lumen configured to accept an endoscope for viewing the bladder.

14. The medical injection assembly of claim 13, further comprising a scope seal positioned at a proximal portion of said endoscope lumen, said scope seal being comprised of a material with a coefficient of friction sufficient to hold in place an endoscope inserted in said endoscope lumen to view the bladder.

15. The medical injection assembly of claim 8, further comprising a cannula seal positioned at a proximal portion of said cannula lumen, said cannula seal being comprised of a material with a coefficient of friction sufficient to hold said cannula in place.

16. A medical assembly comprising:

a hollow cannula having a distal portion with a predefined curvature relative to a straight axis in the absence of a deforming force acting thereon, wherein said predefined curvature is defined by an inverse tangent function;

wherein said distal portion is made of a biocompatible thermoplastic polymer and;

(i) conforms to said straight axis in the presence of said deforming force but (ii) progressively returns to said predefined curvature as a distal tip of the cannula progressively moves distally out of and away from said deforming force;

a hollow injection needle affixed to and extending distally from said distal tip of the cannula;

wherein said injection needle points to injection sites that are radially spaced from each other depending on a distance of the cannula tip and the injection needle from said deforming force and are circumferentially spaced from each other by cannula rotation; and wherein said distal portion of the cannula has a flexural modulus sufficient for inserting the needle into a bladder wall at said injection sites, including when said distal portion of the cannula has returned to said curvature defined by an inverse tangent function, but is sufficiently flexible to extend along said straight axis when in the cannula lumen.

17. The medical assembly of claim 16, further comprising an introducer having a cannula lumen at least a distal portion of which extends along said straight axis and which confines the cannula and exerts said deforming force thereon when said distal portion of the cannula is in said cannula lumen.

18. The medical assembly of claim 17, in which said introducer further comprises an endoscope lumen configured to view a patient's bladder when a distal portion of the introducer is in the bladder.

19. The medical assembly of claim 17, in which an entirety of the cannula lumen extends along said straight axis.

20. The medical assembly of claim 17, in which at least a portion of the cannula lumen matching in length said distal portion of the cannula extends along a linear axis.

21. The medical injection assembly of claim 16, in which said biocompatible thermoplastic polymer is a polyether ether-ketone (PEEK).

22. A method for treating a patient's overactive bladder comprising:

(a) inserting an endoscope into a scope lumen of an introducer;

(b) inserting a hollow, thermoplastic polymer cannula with a hollow needle affixed to and extending distally from a distal end thereof into a cannula lumen of the introducer, thereby causing a least a distal portion of the cannula to conform to a first shape while in the cannula lumen;

(c) coupling a syringe containing onabotulinumtoxina to said cannula;

(d) guiding the introducer through a patient's urethra to the patient's bladder;

(e) distally moving the cannula along the cannula lumen to cause a distal tip of the cannula to extend distally a first selected axial distance away from said cannula lumen, thereby causing a distal portion of the cannula that has moved distally out of the cannula lumen by said first selected distance to return to a second shape that conforms to a curvature that is defined by an inverse tangent function and is different from the first shape, the cannula having had said curvature before being inserted in said cannula lumen, and to cause the cannula tip to be at a first selected radial distance from the cannula lumen;

(f) moving the introducer distally and inserting the needle into the bladder, injecting a selected amount of onabotulinumtoxina into a bladder wall at an injection site using said syringe, withdrawing the needle from the bladder, rotating the cannula to thereby point the needle to another injection site, moving the introducer distally and injecting another selected amount of onabotulinumtoxina into the bladder wall, at a site circumferentially spaced from the site of the preceding injection, and repeating step (f) a selected number of times; and (g) moving the cannula along said cannula lumen to cause the cannula tip to extend distally away from the cannula lumen by a second selected distance, to thereby cause the cannula tip to be at a second radial distance that is different from the first radial distance, and repeating step (f);

(h) thereby injecting a therapeutically effective amount of onabotulinumtoxina in a therapeutically effective pattern of injection sites in the bladder wall; and providing the cannula with a flexural modulus sufficient for inserting the needle into bladder tissue, including when the curvature thereof conforms to an inverse tangent function, and with sufficient flexibility to assume said first shape when in the cannula lumen.

23. The method of claim 22 in which said using of the syringe to inject comprises providing a syringe with detents along an axis in which a syringe plunger body moves in a syringe barrel and tabs interacting with said detents to provide a tactile indication of a predetermined motion of the plunger body relative to the syringe barrel corresponding to the injection of said predetermined amount of onabotulinumtoxina.

* * * * *